United States Patent
Abraham et al.

(10) Patent No.: US 10,107,766 B2
(45) Date of Patent: Oct. 23, 2018

(54) PHOTON COUNTING IMAGING MODES

(71) Applicant: Analogic Corporation, Peabody, MA (US)

(72) Inventors: Doug Q. Abraham, Topsfield, MA (US); Anton Deykoon, Arlington, MA (US); Basak Ulker Karbeyaz, Concord, MA (US)

(73) Assignee: Analogic Corporation, Peabody, MA (US)

( * ) Notice: Subject to any disclaimer, the term of this patent is extended or adjusted under 35 U.S.C. 154(b) by 280 days.

(21) Appl. No.: 14/597,756

(22) Filed: Jan. 15, 2015

(65) Prior Publication Data
US 2016/0209338 A1    Jul. 21, 2016

(51) Int. Cl.
*G01N 23/087* (2018.01)

(52) U.S. Cl.
CPC ..... *G01N 23/087* (2013.01); *G01N 2223/423* (2013.01)

(58) Field of Classification Search
CPC ............... H01L 31/107; H01L 31/0232; H01L 31/0352; H01L 31/02162; H01L 31/02005; H01L 31/02327; H01L 31/23046; G01N 23/087; G06T 11/005
See application file for complete search history.

(56) References Cited

U.S. PATENT DOCUMENTS

| | | | |
|---|---|---|---|
| 9,207,332 B2* | 12/2015 | Spahn | G01T 1/17 |
| 2007/0147579 A1* | 6/2007 | De Man | A61B 6/032 378/16 |
| 2007/0267710 A1* | 11/2007 | Raynor | H04N 3/155 257/431 |
| 2010/0215230 A1* | 8/2010 | Bornefalk | G06T 11/005 382/128 |
| 2014/0185749 A1* | 7/2014 | Lee | G06T 11/006 378/41 |

* cited by examiner

*Primary Examiner* — David E Smith
*Assistant Examiner* — Hsien Tsai
(74) *Attorney, Agent, or Firm* — TraskBritt

(57) ABSTRACT

Among other things, one or more techniques and/or systems are described for defining imaging modes and for operating a photon counting radiation imaging system. A set of imaging modes with different counting schemes may be defined such that counting schemes will count detection events of a set of radiation events in different manners. For example, a first counting scheme may count primary detection events in a primary counter and secondary detection events in a secondary counter. A second counting scheme may count primary and secondary detection events in the primary counter. A third counting scheme may merely count detection events occurring within a primary detector cell associated with the primary counter. A fourth counting scheme may combine energy of detection events into merged energy. A selected imaging mode may be applied to the photon counting radiation imaging system in order to achieve desired image scanning characteristics (e.g., spatial resolution, dose savings, spectral ability).

20 Claims, 8 Drawing Sheets

PHOTON COUNTING IMAGING MODES

TECHNICAL FIELD

The present application relates to the field of radiation imaging systems. It finds particular application to data acquisition systems of radiation imaging systems that use photon counting detector arrays to measure a number and/or energy of radiation photons impinging thereon.

BACKGROUND

Today, radiation imaging systems such as computed tomography (CT) systems, single-photon emission computed tomography (SPECT) systems, projection systems, and/or line-scan systems, for example, are useful to provide information, or images, of interior aspects of an object under examination. Generally, the object is exposed to radiation comprising photons (e.g., X-rays, gamma rays, etc.), and an image(s) is formed based upon the radiation absorbed and/or attenuated by interior aspects of the object, or rather an amount of radiation photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation imaging systems typically comprise a detector array having one or more detector cells. Respective detector cells are configured to indirectly or directly convert radiation photons impingent thereon into electrical charge, which is used to generate an electrical signal. The detector cells are typically "energy integrating" or "photon counting" type detector cells (e.g., the radiation imaging system operates in energy integrating mode or photon counting mode).

Energy integrating detector cells are configured to integrate the electrical charge generated over a period of time (e.g., at times referred to as a measurement interval or view) to generate a signal that is proportional to an incoming radiation photon flux rate at a detector cell. While energy integrating detector cells are widely used, there are several drawbacks to this type of cell. For example, energy integrating detectors cells are generally not able to provide feedback as to the number and/or energy of radiation photons detected. As another drawback, there is a lower limit of detection defined by noise such that a detector cell with little to no incident radiation may produce some signal due to thermal and/or analog read noise (e.g., produced by a radiation detection element and/or electronics arrangement of the detector cell). It may be appreciated that as a result of this lower limit, the dose of radiation that is applied to an object under examination is generally greater than the dose of radiation that may be applied to the object if the detector cells are of a photon counting type.

Photon counting type detector cells are configured to output a signal (e.g., a pulse) for respective detected radiation photons (e.g., where the detection of a radiation photon may be referred to as a detection event). In some embodiments, the signal (e.g., or an amplitude of the pulse) is indicative of a radiation energy of the detected radiation photon. A controller is configured to determine the location and energy of respective detected radiation photons based upon the pulse, accumulate the detection events occurring during a measurement interval, digitize the information, and/or process the digital information to form an image, for example. It may be appreciated that there are numerous advantages to photon counting type detector cells over energy integrating detector cells. For example, the counting of radiation photons is essentially noise free (e.g., apart from inherent photon shot noise). Therefore, a lower dose of radiation may be applied to the object under examination. Moreover, photon counting cells generally allow for energy or wavelength discrimination.

BRIEF SUMMARY

Aspects of the present application address the above matters, and others. According to one aspect, a method for defining imaging modes is provided. The method comprises defining a first imaging mode for counting detection events of a photon counting radiation imaging system. The method also comprises defining a second imaging mode for counting detection events of the photon counting radiation imaging system. The first imaging mode has a first counting scheme and the second imaging mode has a second counting scheme different than the first counting scheme.

According to another aspect, a photon counting radiation imaging system is provided. The photon counting radiation imaging system comprises a radiation source configured to emit radiation and a detector array comprising a plurality of detector cells respectively configured to count detection events. The photon counting radiation imaging system also comprises a mode selection component configured to select an imaging mode for the detector cells. A first imaging mode has a first counting scheme and a second imaging mode has a second counting scheme different than the first counting scheme.

According to yet another aspect, a method for operation of a photon counting radiation imaging system is provided. The method comprises determining a type of object that is being imaged by the photon counting radiation imaging system and selecting an imaging mode for counting detection events of the photon counting radiation imaging system based upon the type of object.

Those of ordinary skill in the art will appreciate still other aspects of the present application upon reading and understanding the detailed description.

BRIEF DESCRIPTION OF THE DRAWINGS

The application is illustrated, by way of example and not limitation, in the figures of the accompanying drawings, in which like references generally indicate similar elements and in which.

DETAILED DESCRIPTION

Figure 1:
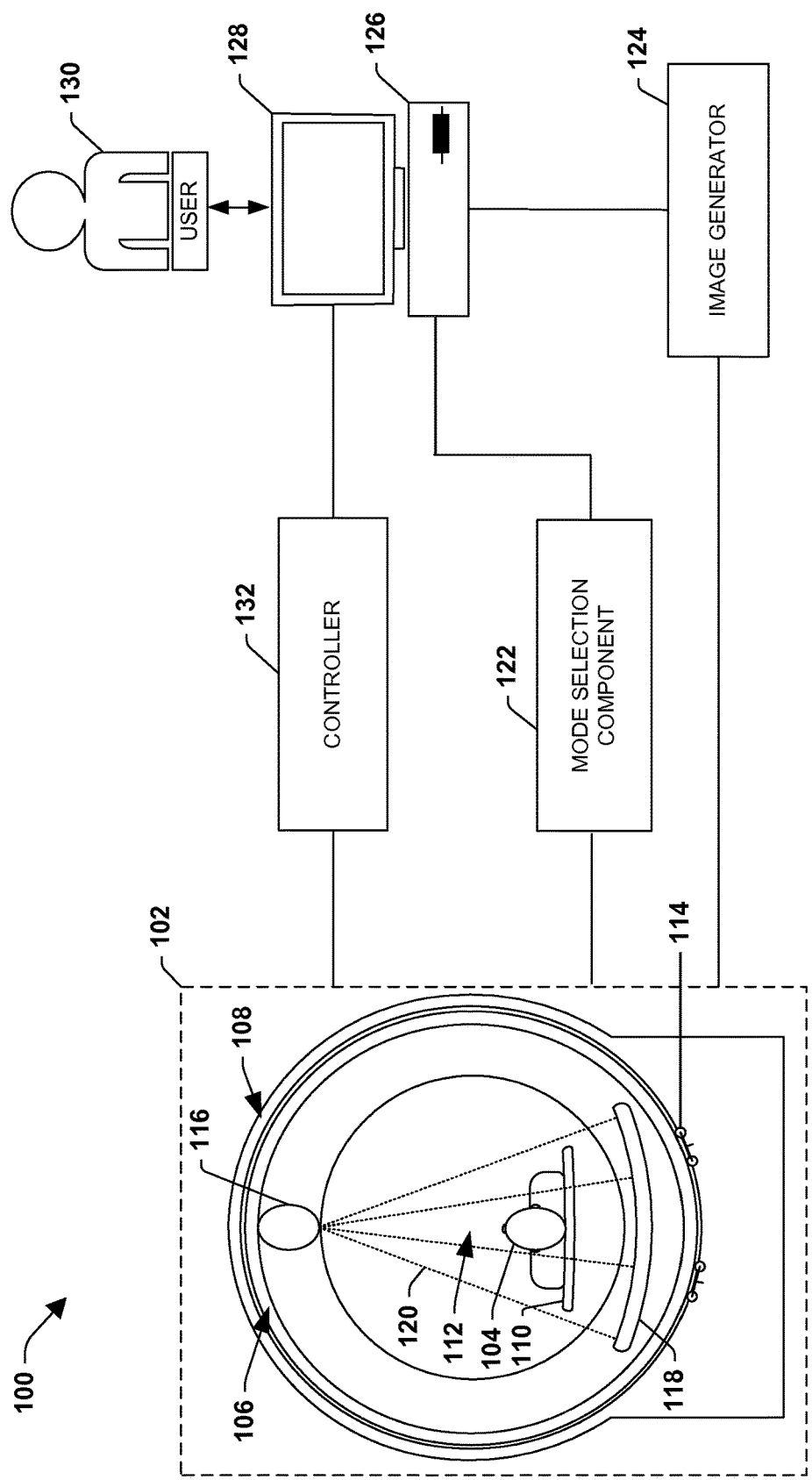
FIG. 1 illustrates an example environment of a photon counting radiation imaging system.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

While photon counting type detector cells offer numerous benefits over charge integrating type detector cells, scattering has a greater impact on images resulting from photon counting than on images resulting from charge integration. When the detector cells are configured to directly convert radiation photons into electrical charge, scattering refers to the Compton scatter of impinging radiation photons or to photoelectric absorption of the impinging radiation photons followed by emission of a characteristic photon. In both scatter events, a fraction of the energy corresponding to an incident radiation photon is converted to electrical charge at the point of impact, while another fraction of the energy is transferred via secondary radiation to another location, which may be hundreds of microns away from the point of impact, for example. The secondary radiation may convert to electrical charge in a neighboring detector cell(s) (e.g., detector cells neighboring the detector cell upon which the radiation photon impinged), causing the detector array to identify multiple detection events (e.g., at a single detector cell or within a neighborhood of detector cells) for a single radiation photon.

According to some embodiments, imaging modes are created that define how detection events attributable to scattering are to be processed/counted by a photon counting radiation imaging system. As used herein, a photon counting radiation imaging system refers to a radiation imaging system having photon counting type detector cells and thus configured to count photons. In some embodiments, an operator of the photon counting radiation imaging system may select an imaging mode when examining an object based upon desired properties of an image(s) resulting from the examination, for example. In some embodiments, the photon counting radiation imaging system may programmatically select the imaging mode based upon the type of object being examined.

Respective imaging modes use a different counting scheme, which may result in images having different image characteristics, having different dose requirements, and/or having differing degrees of spectral ability depending upon the imaging mode selected. For example, a first imaging mode may provide higher spatial resolution images than a second imaging mode, but the first imaging mode may require the object to be exposed to more radiation than required by the second imaging mode. Selection of an imaging mode may comprise balancing spatial resolution of resulting images with a radiation dose, for example.

As used herein a radiation event refers to the conversion of a radiation photon into electrical charge (e.g., which may occur in a radiation detection element (e.g., direct conversion material) of respective detector cells) and a detection event refers to the detection of electrical charge yielded from a radiation event (e.g., which may occur at an electronics arrangement (e.g., readout element) of respective detector cells). A detection event that occurred earlier in time (e.g., detected first by an anode) is called a primary event, and the detector cell in which the primary detection event occurred is referred to as a primary detector cell. If scatter is present, a primary detection event may be followed by one or more secondary detection events, which may occur in the primary detector cell and/or one or more secondary detector cells neighboring the primary cell. In some instances, the primary detector cell for a radiation event may be the detector cell that the radiation photon initially impinged. In other instances, the primary detector cell for a radiation event may be a detector cell that the radiation photon did not initially impinge because a primary cell measurement can occur from scatter radiation.

It may be appreciated that a secondary detection event may be distinguishable from a second primary detection event due to, among other things, the temporal proximity of the second detection event relative to the primary detection event. For example, if a second detection event is detected nearly immediately after the primary detection event (e.g., and is detected by the same detector cell or a neighboring detector cell), the second detection event is likely to be a secondary detection event (e.g., caused due to scatter of the radiation photon). If there is at least some specified period of delay between the second detection event and the primary detection event, the second detection event is likely to be indicative of a second primary detection event (e.g., due to another radiation photon) as opposed to a secondary detection event.

FIG. 1 illustrates a photon counting radiation imaging system 100. In the illustrated embodiment, the photon counting radiation imaging system 100 is a computed tomography (CT) system, although the systems and/or techniques described herein may find applicability to other photon counting radiation imaging systems such as line-scan systems, mammography systems, and/or diffraction systems, for example. Moreover, it may be appreciated that the arrangement of features, inclusion of features and/or exclusion of other features from the example photon counting radiation imaging system 100 is not intended to be interpreted in a limiting manner, such as necessarily specifying the location, inclusion, and/or relative position of the features.

The example photon counting radiation imaging system 100 comprises an examination unit 102 configured to an examine objects 104. The examination unit 102 comprises a rotating gantry 106 and a (e.g., stationary) support structure 108 (e.g., which may encase and/or surround at least a portion of the rotating gantry 106 (e.g., as illustrated with an outer, stationary ring, surrounding an outside edge of an inner, rotating ring)). The examination unit 102 also comprises a support article 110, such as a bed or conveyor belt, configured to support the object 104 during an examination. In some embodiments, the support article 110 may be configured to translate the object into and/or through an examination region 112 (e.g., a hollow bore in the rotating gantry 106), where the object 104 is exposed to radiation 120, during the examination. The object 104 may be an animal, human, or inanimate object (e.g., baggage).

The rotating gantry 106 may surround a portion of the examination region 112 and may comprise a radiation source 116 (e.g., an ionizing radiation source such as an X-ray source or gamma-ray source) and a detector array 118. The detector array 118 is typically mounted on a substantially diametrically opposite side of the rotating gantry 106 relative to the radiation source 116, and during an examination of the object 104, the rotating gantry 106 (e.g., including the radiation source 116 and detector array 118) is rotated about the object 104 by a rotator 114 (e.g., belt, drive shaft, chain, roller truck, etc.). Because the radiation source 116 and the detector array 118 are mounted to the rotating gantry 106, a relative position between the detector array 118 and the radiation source 116 is substantially maintained during the rotation of the rotating gantry 106.

During the examination of the object 104, the radiation source 116 emits cone-beam and/or fan-beam radiation 120 from a focal spot of the radiation source 116 (e.g., a region within the radiation source 116 from which the radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or multi-energy spectrums depending upon, among other things, whether the photon counting radiation imaging system 100 is configured as a single-energy system or a multi-energy (e.g., dual-energy) system.

As the emitted radiation 120 traverses the object 104, the radiation 120 may be attenuated (e.g., absorbed and/or scattered) differently by different aspects of the object 104. Because different aspects attenuate different percentages of the radiation 120, the number of photons detected by respective detector cells of the detector array 118 may vary. For example, detector cells that are shadowed by dense aspects of the object 104, such as a bone or metal plate, may detect fewer radiation photons (e.g., or a ratio between high energy radiation photons and low energy radiation photons may be higher) than detector cells that are shadowed by lower density aspects of the object 104, such as skin or clothing (e.g., which may allow an overall greater number of radiation photons to pass through and/or may allow a greater number of low energy radiation photons to pass through).

Respective detector cells of the detector array 118 may comprise a radiation detection element and an electronics arrangement (e.g., a data acquisition system (DAS)). The radiation detection element is configured to directly convert radiation photons into electrical charge and the electronics arrangement is configured to generate an analog signal based upon the detection events.

The radiation detection element of respective detector cells generally comprises a conversion material configured to convert the radiation photons into electrical charge. Example conversion materials of a direct conversion detector array include, among other things, Cadmium Zinc Telluride, Cadmium Telluride, Silicon, and/or an amorphous material.

The electronics arrangement of respective detector cells is generally configured to convert the electrical charge into an electrical signal and/or process the electrical signal (e.g., via readout circuitry). Such processing may include filtering, shaping, and/or measuring the electrical signal to generate useful information regarding respective detection events on a detector cell, such as a number of detection events counted by respective detector cells. A counting scheme, implemented in counting logic of the electronics arrangement, for example, may be used to define how the detection events are counted by respective detector cells and/or by the detector array 118. For example, the counting scheme may specify how respective detector cells are to handle primary detection events that occur within a primary detector cell and/or secondary detection events that occur within the primary detector cell and/or within one or more secondary detector cells.

In the example photon counting radiation imaging system 100, a mode selection component 122 is configured to define the counting scheme based upon an imaging mode selected for an examination. As will be described in more detail below, the imaging mode may be user-selectable and/or may be programmatically selected, such as based upon the object 104 under examination. By way of example, a user may select a particular imaging mode from an imaging mode selection user interface displayed through a monitor 128 of a terminal 126 of the photon counting radiation imaging system 100. In another example, an imaging mode may be selected based upon a type of object that is to be scanned, such as by using object recognition functionality that may distinguish between a lung and other body parts from a pre-scan image based upon atomic signatures, shapes, blood vessel patterns, etc.

Information generated and/or compiled by the electronics arrangement (e.g., such as a number of detection events detected by respective detector cells according to the counting scheme applied) may be transmitted to an image generator 124 configured to generate an image(s) of the object 104 using the information. Such images may depict a two-dimensional representation of the object 104 and/or a three-dimensional representation of the object 104. In other embodiments, the information may be transmitted to other digital processing components, such as a threat analysis component, for processing.

The example photon counting radiation imaging system 100 also includes the terminal 126, or workstation (e.g., a computer), configured to receive image(s) from the image generator 124, which can be displayed on a monitor 128 to a user 130 (e.g., security personnel, medical personnel, etc.). In this way, the user 130 can inspect the image(s) to identify areas of interest within the object(s) 104. The terminal 126 can also be configured to receive user input, which can direct operations of the examination unit 102 (e.g., a speed of gantry rotation, an energy level of the radiation, an imaging mode, etc.).

In the example photon counting radiation imaging system 100, a controller 132 is operably coupled to the terminal 126. The controller 132 may be configured to control operations of the examination unit 102, for example. By way of example, in some embodiments, the controller 132 may be configured to receive information from the terminal 126 and to issue instructions to the examination unit 102 indicative of the received information (e.g., adjust a speed of a conveyor belt, adjust a voltage applied to the radiation source 116, etc.).

Figure 2:
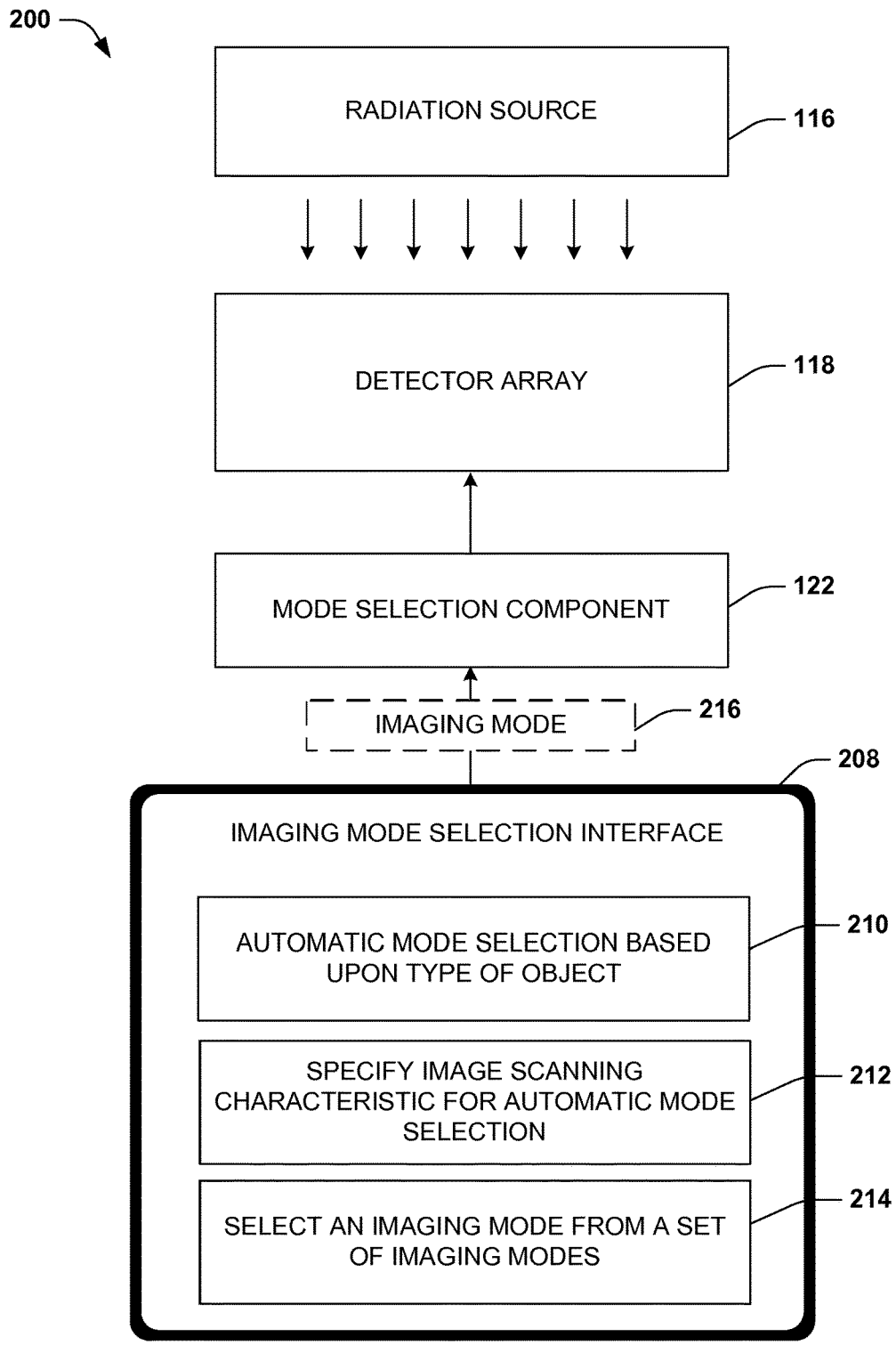
FIG. 2 illustrates a schematic diagram of an example photon counting radiation imaging system.

Referring to FIG. 2, a schematic diagram of at least some components of a photon counting radiation imaging system 100 is illustrated. The photon counting radiation imaging system 100 comprises a radiation source 116, a detector array 118, and/or a mode selection component 122. The mode selection component 122 is configured to display an image mode selection interface 208 (e.g., through the monitor 128 of the terminal 126). In an example, the type of object may be determined based upon user input (e.g., the user may specify that a lung is to be scanned).

In another example, the mode selection component 122 may populate the image mode selection interface 208 with an automatic mode selection option 210 used to select an imaging mode based upon a type of object that is to be scanned. Responsive to selection of the automatic mode selection option 210, the mode selection component 122 may determine a type of object that is being imaged by the photon counting radiation imaging system 200. The mode selection component 122 may select an imaging mode for counting detection events of the photon counting radiation imaging system 200 based upon the type of object (e.g., a selected imaging mode may provide a desired spatial resolution of images depicting the type of object; the selected imaging mode may be based upon a sensitivity of the object to radiation; etc.). In an example, the type of object may be determined based upon a pre-scan of the object (e.g., object recognition may be used to identify the object features, such as an atomic signature, a pattern of blood vessels, a shape, or other features of an object). In another example, the type of object may be determined based upon an analysis of a previously acquired image (e.g., object recognition may be used to identify the object features, such as an atomic signature, a pattern of blood vessels, a shape, or other features of an object).

In an example, the mode selection component 122 may populate the image mode selection interface 208 with an image scanning characteristics automatic mode selection option 212. Responsive to selection of the image scanning characteristics automatic mode selection option 212, a set of image scanning characteristics may be displayed. The user may select and/or specify varying degrees of importance for image scanning characteristics (e.g., a desired spatial resolution of images, a sensitivity to radiation, etc.), which may be used to identify a corresponding imaging mode that is configured to generate images having such image scanning characteristics (e.g., a first imaging mode may be selected because the first imaging mode may provide medium spatial resolution, high dose savings, and minimal spectral ability).

In an example, the mode selection component 122 may populate the image mode selection interface 208 with an imaging mode selection option 214. Responsive to selection of the imaging mode selection option 214, a set of imaging modes may be displayed for user selection of an imaging mode. For example, the set of imaging modes may comprise a first imaging mode having a first counting scheme in which a secondary detection event, detected by a secondary detector cell, is counted in a secondary counter associated with the secondary detector cell (e.g., a corresponding primary event may be counted by a primary counter associated with a primary detector cell, and secondary events may be detected by respective secondary counters). The set of imaging modes may comprise a second imaging mode having a second counting scheme in which a secondary detection event is counted in the primary counter associated with the primary detector cell instead of the secondary counter associated with the secondary detector cell (e.g., secondary detection events are counted in the primary counter and not secondary counters). The set of imaging modes may comprise a third imaging mode having a third counting scheme in which primary detection events and secondary detection events occurring within the primary detector cell are counted while secondary detection events occurring within secondary detector cells not counted. The set of imaging modes may comprise a fourth imaging mode having a fourth counting scheme in which first energy associated with a primary detection event and second energy associated with a secondary detection event are merged to generate a merged energy. As will be described in more detail with respect to FIGS. 3-6, such counting schemes may count detection events of a set of radiation events differently. In this way, an imaging mode 216 may be determined.

The mode selection component 122 may apply the imaging mode 216 to the photon counting radiation imaging system 200. For example, the mode selection component 122 may select or modify counting logic associated with the detector array 118. In this way, radiation photons from the radiation source 116 may be detected by the detector array 118 and counted by the counting logic based upon the imaging mode 216.

Figure 3:
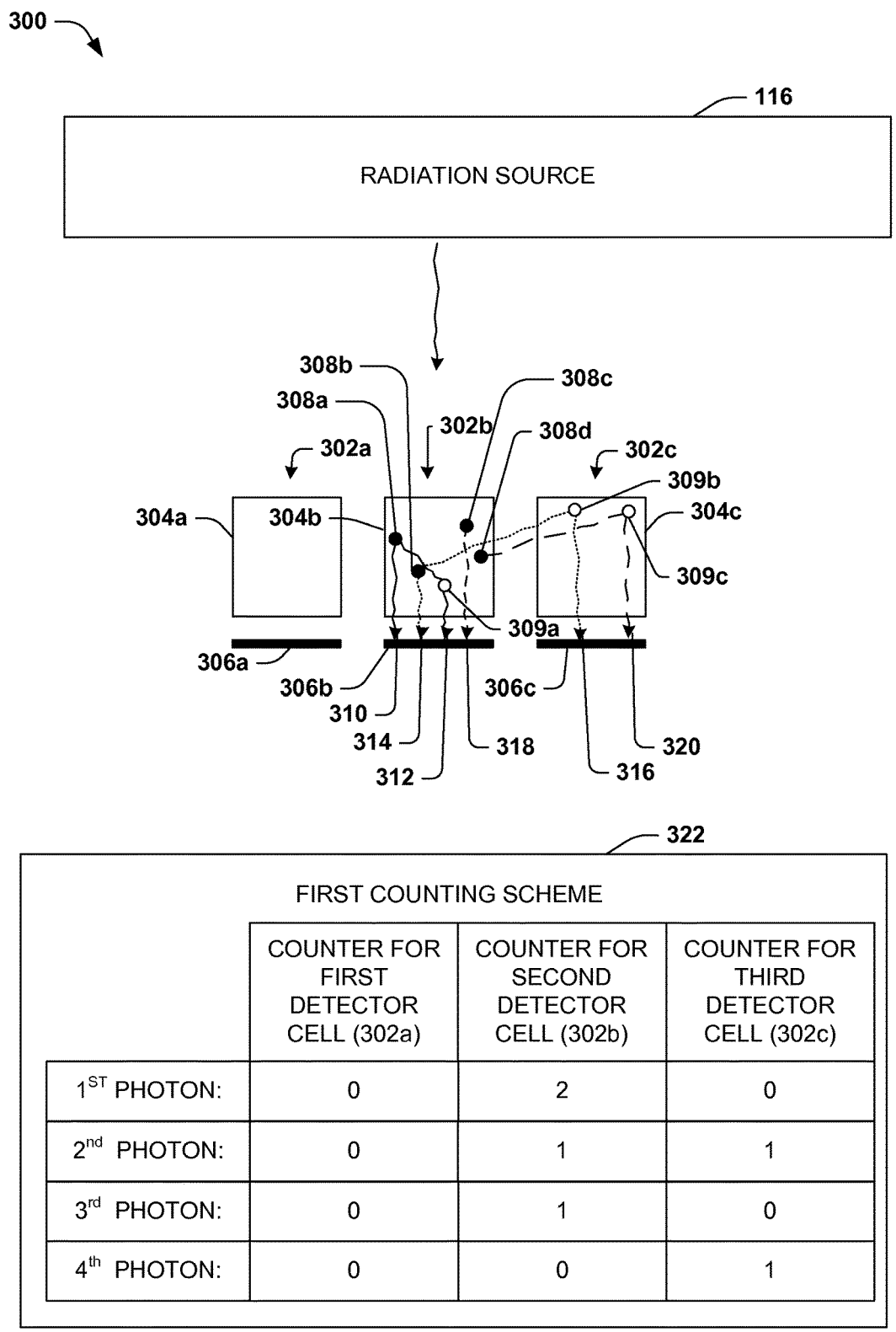
FIG. 3 illustrates an example of applying a first counting scheme to a photon counting radiation imaging system.

FIG. 3 illustrates an example 300 of implementing a first counting scheme 322 of a first imaging mode. The radiation source 116 emits radiation photons that are detected by detector cells of the detector array 118. Respective detector cells 302 comprise a conversion material 304 configured to convert radiation photons impinging thereon into electrical charge and an electronics arrangement 306 configured to detect and/or measure the electrical charge and to generate an electrical pulse in response thereto. In some embodiments, the amount of electrical charge generated from a radiation event is proportional to an energy of the radiation photon and the amplitude of the pulse, for example, is a function of the amount of electrical charge detected during a sampling period (e.g., which may be proportional to the energy of the radiation photon). In this way, in some embodiments, spectral information regarding the energy of a radiation photon may be determined from the electrical pulse. The amplitude of the pulse may correspond to the voltage or the current of the pulse, for example.

To demonstrate how the first counting scheme 322 of the second imaging mode may function, consider four representative radiation events, in which various patterns of electrical charge generated in response to various radiation events are illustrated. The black-filled circles represent a location where radiation photons impinged the detector array and the white-filled circles represent a location where secondary radiation photons, yielded from the impinging radiation photons, were converted into electrical charge.

It is to be appreciated that the radiation photons 308 initially impinged a second detector cell 302b of the detector array before being scattered to other detector cells, such as the third detector cell 302c. The second detector cell 302b transforms a first radiation photon 308a into first electrical charge (e.g., represented by the solid squiggly lines) during a first radiation event. A first portion 310 of the first electrical charge is generated at a location where the first radiation photon 308a deposited some energy. A second portion 312 of the first electrical charge is generated at a location where a secondary radiation photon 309a, generated from the first radiation photon 308a due to scattering, deposited some energy. In this instance, the second portion 312 of the first electrical charge is detected within the second detector cell 302b, and thus energy associated with the first radiation photon 308a is not shared with other detector cells, such as the first detector cell 302a and/or the third detector cell 302c. As a result, the second detector cell 302b detects two radiation photons as detection events corresponding to the first radiation event. The detection event of these two detection events that is detected first by the second detector cell 302 may be referred to as a primary detection event and the other detection event may be referred to as a secondary detection event. Irrespective of which of these two detection events are detected first, the second detector cell 302b is the primary detector cell because both of the two detection events occurred within the second detector cell 302b.

The second detector cell 302b transforms a second radiation photon 308b into second electrical charge (e.g., represented by the dotted squiggly lines) during a second radiation event. A first portion 314 of the second electrical charge is generated at a location where the second radiation photon 308b deposited some energy and remains in the second detector cell 302b. A second portion 316 of the second electrical charge is generated at a location where a secondary radiation photon 309b, generated from the second radiation photon 308b due to scattering, deposited some energy. In this instance, the second portion 316 of the second electrical charge is detected within the third detector cell 302c. As a result, the second detector cell 302b detects a first detection event corresponding to the second radiation event and the third detector cell 302c detects a second detection event corresponding to the second radiation event. The first detection event may be referred to as a primary detection event if the second detector cell 302b detected the first portion 314 of the second electrical charge before the third detector cell 302c detected the second portion 316 of the second electrical charge. Thus, in this scenario, the second detector cell 302b is the primary detector cell and the third detector cell 302c is a secondary detector cell for the second radiation photon 308b.

The second detector cell 302b transforms a third radiation photon 308c into a third electrical charge 318 (e.g., represented by the medium sized dash line) during a third radiation event. In this instance, there is no scatter (e.g., the charge detected in the second detector cell 302b corresponds to the full energy of the incident radiation photon 308c). As a result, the second detector cell 302b detects merely a first detection event corresponding to the third radiation event. This first detection event may be referred to as a primary detection event.

The second detector cell 302b interacts with a fourth radiation photon 308d during a fourth radiation event, although little to no energy is deposited in the second cell 302b by the fourth radiation photon 308d. Rather, the fourth radiation photon 308d is scattered (e.g., almost entirely) into the third detector cell 302c as represented by the secondary radiation photon 309c. Thus, energy from the fourth radiation photon 308d is deposited in the third detector cell 302c (e.g., via the secondary radiation photon 309c) to generate a fourth electrical charge 320. As a result, the third detector cell 302c detects a first detection event corresponding to the fourth radiation event and the second detector cell 302b detects no detection event corresponding to the fourth radiation event. This first detection event may be referred to as a primary detection event for the fourth radiation photon 308d and the third detector cell 302c will be the primary detector cell for the fourth radiation photon 308d.

The first counting scheme 322 may specify that, for respective detection events, respective detection events are to be counted by the counter where the detection event occurred. Thus, a counter associated with the second detector cell 302b may count two detection events for the first radiation event, one detection event for the second radiation event, one detection event for the third radiation event, and zero detection events for the fourth radiation event. A counter associated with the third detector cell 302c may count zero detection events for the first radiation event, one detection event for the second radiation event, zero detection events for the third radiation event, and one detection event for the fourth radiation event. It may be appreciated that due to multiple detection events (e.g., in multiple detector cells) being counted for a single radiation event, little to no spectral information about the radiation photon associated with the radiation event may be determined using the first counting scheme 322. Moreover, it may be appreciated that while radiation photons are illustrated as being scattered to merely one secondary detector cell, radiation photons associated with a radiation event may be scattered to a plurality of detector cells that are a first-order neighbor of the primary detector cell, a second-order neighbor of the primary detector cell, etc.

Figure 4:
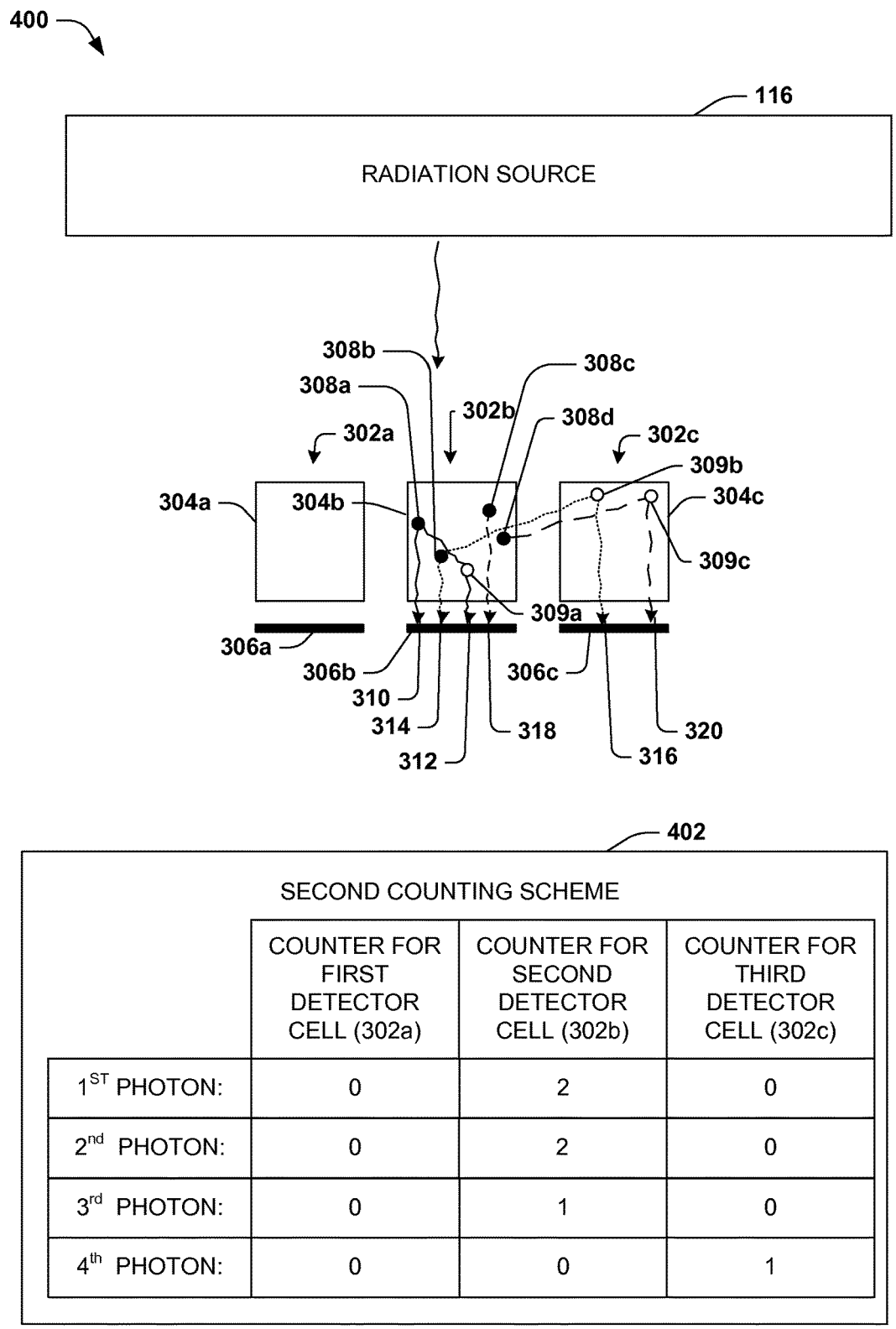
FIG. 4 illustrates an example of applying a second counting scheme to a photon counting radiation imaging system.

FIG. 4 illustrates an example 400 of implementing a second counting scheme 402 of a second imaging mode. The second counting scheme 402 may specify that primary detection events and secondary detection events, occurring at the primary detector cell and/or any secondary detector cells, are to be counted by the counter associated with the primary detector cell.

To demonstrate how the second counting scheme 402 of the second imaging mode may function, consider the four example radiation events described with respect to FIG. 3 (e.g., and reproduced in FIG. 4), in which various patterns of electrical charge generated in response to various radiation events are illustrated. According to the second counting scheme 402, a counter associated with the second detector cell 302b may count two detection events for the first radiation event, two detection events for the second radiation event (e.g., because the secondary detection event, associated with the second radiation event and detected at the third detector cell 302c, is counted by the counter associated with the second detector cell 302b), one detection event for the third radiation event, and zero detection events for the fourth radiation event. The fourth radiation photon 308d is counted as one radiation event in the third detector cell 302c because the third detector cell 302c is the primary detector cell for the fourth radiation photon 308d. It may be appreciated that due to multiple detection events being counted for a single radiation event, little to no spectral information about the radiation photon associated with the radiation event may be determined using the second counting scheme 402.

Figure 5:
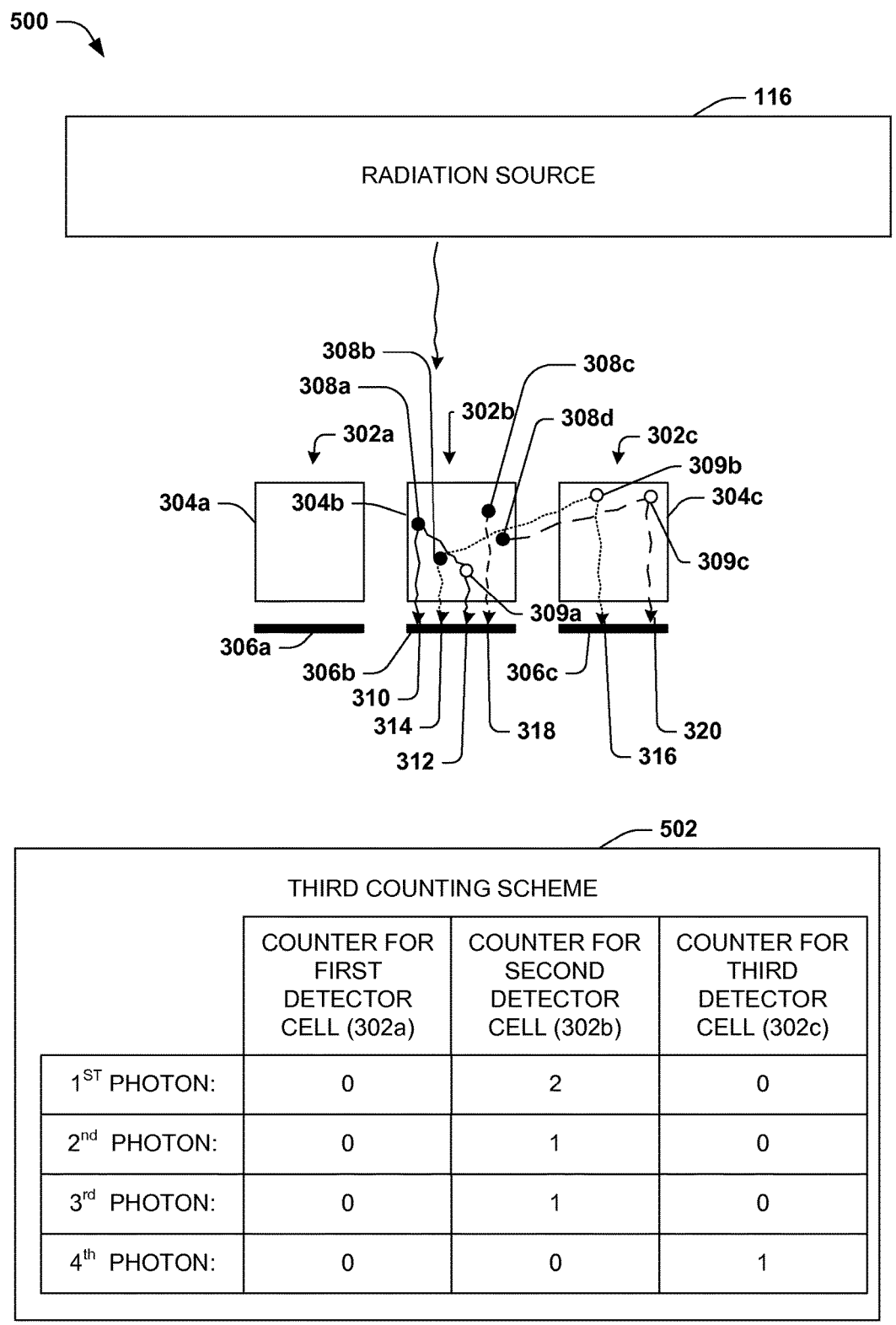
FIG. 5 illustrates an example of applying a third counting scheme to a photon counting radiation imaging system.

FIG. 5 illustrates an example 500 of implementing a third counting scheme 502 of a third imaging mode. The third counting scheme 502 may specify that primary detection events and secondary detection events occurring within the primary detector cell are to be counted. Secondary detection events occurring within secondary detector cells are not to be counted.

To demonstrate how the third counting scheme 502 of the third imaging mode may function, consider the four example radiation events described with respect to FIG. 3 (e.g., and reproduced in FIG. 5), in which various patterns of electrical charge generated in response to various radiation events are illustrated. According to the third counting scheme 502, a counter associated with the second detector cell 302b may count two detection events for the first radiation event, one detection event for the second radiation event (e.g., the secondary detection event, associated with the second radiation event and detected at the third detector cell 302c, is not counted), one detection event for the third radiation event, and zero detection events for the fourth radiation event. The fourth radiation photon 308d is scattered into the third detector cell 302c, which is the primary detector cell for the fourth radiation photon 308d because no electrical charge was deposited at the second detector cell 302b (e.g., and thus no detection event occurred at the second detector cell 302b). It may be appreciated that due to secondary detection events being disregarded, little to no spectral information about the radiation photon associated with the radiation event may be determined using the third counting scheme 502.

Figure 6:
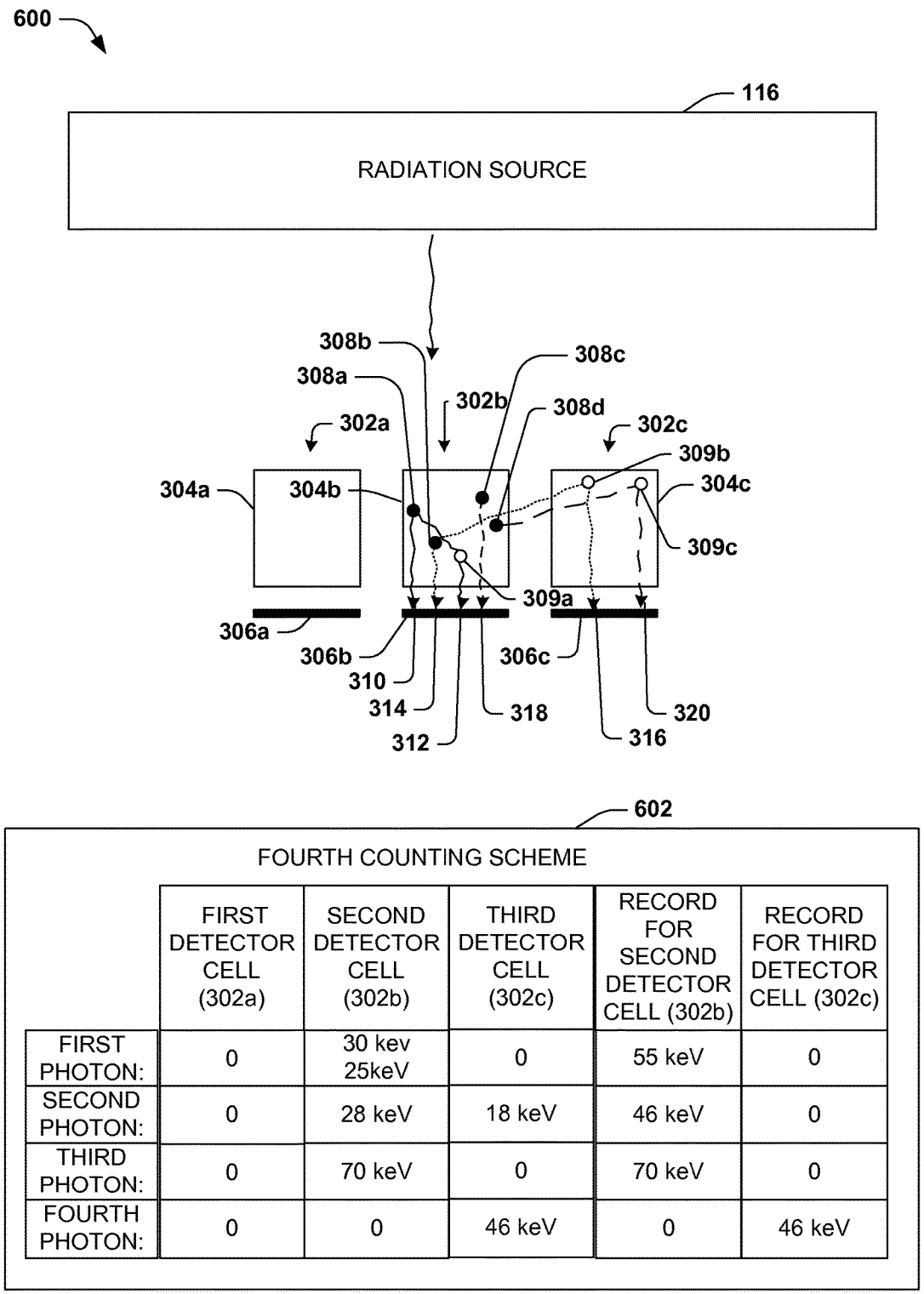
FIG. 6 illustrates an example of applying a fourth counting scheme to a photon counting radiation imaging system.

FIG. 6 illustrates an example 600 of implementing a fourth counting scheme 602 of a fourth imaging mode. The fourth counting scheme 602 may specify that energy information associated with respective detection events for a same radiation event are to be merged together to generate a merged energy, which is recorded at the primary detector cell for the radiation event.

To demonstrate how the fourth counting scheme 602 of the fourth imaging mode may function, consider the four example radiation events described with respect to FIG. 3 (e.g., and reproduced in FIG. 6), in which various patterns of electrical charge generated in response to various radiation events are illustrated. For respective detection events, the detector cell 302 may be configured to determine an energy level or energy spectrum of the radiation photon based upon the amount of charge corresponding to the detection event. By way of example, the second detector cell 302*b* may have detected approximately 30 keV of energy for the primary detection event associated with first radiation event and may have detected approximately 25 keV of energy for the secondary detection event associated with the first radiation event. Information regarding these two detection events, including their respective energies, may be merged to determine a total energy of 55 keV associated with the first radiation event, which may be recorded in a record associated with the second detector cell 302*b* as a merged energy. As another example, the second detector cell 302*b* may have detected approximately 28 keV of energy for the primary detection event associated with second radiation event and the third detector cell 302*c* may have detected approximately 18 keV of energy for the secondary detection event associated with the second radiation event. Information regarding these two detection events, including their respective energies, may be merged to determine a total energy of 46 keV associated with the second radiation event, which may be recorded in the record associated with the second detector cell 302*b* as a merged energy. As yet another example, the second detector cell 302*b* may have detected approximately 70 keV of energy for the primary detection event associated with the third radiation event, which may be recorded in the record associated with the second detector cell 302*b* as a merged energy. As still another example, the third detector cell 302*c* may have detected approximately 46 keV of energy for the secondary detection event associated with the fourth radiation event, and is registered in the third detector cell 302*c*, which may be recorded in a record associated with the third detector cell 302*c* because the third detector cell 302*c* is the primary detector cell for the fourth radiation event.

Figure 7:
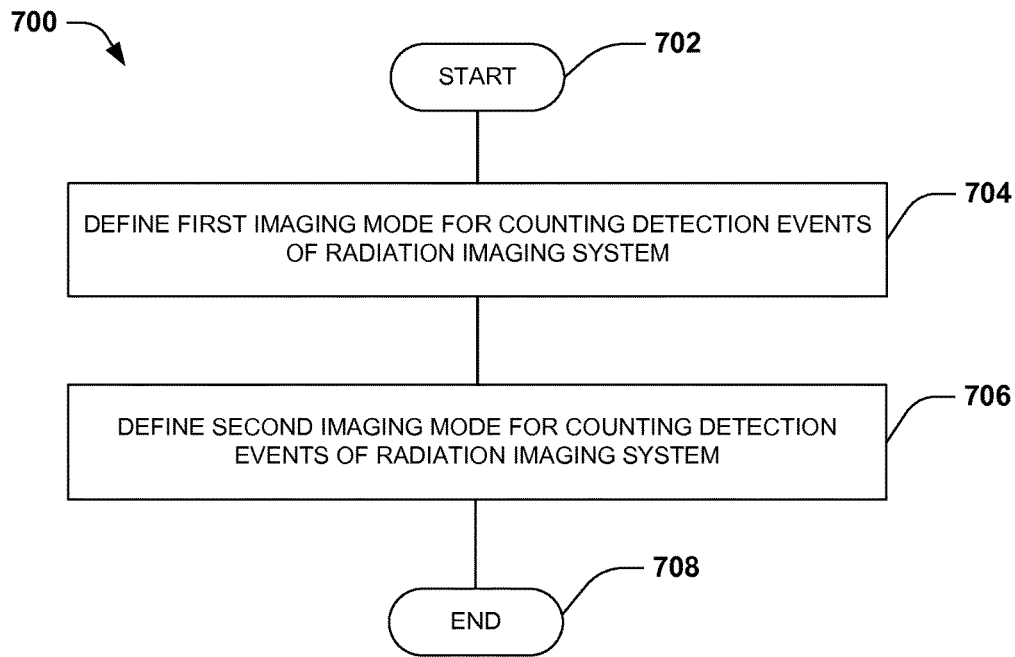
FIG. 7 is a flow diagram illustrating an example method for defining imaging modes.

Referring to FIG. 7, a flow diagram of an example method 700 for defining imaging modes is provided.

The example method 700 starts at 702, and a first imaging mode for counting detection events of a photon counting radiation imaging system is defined, at 704. At 706, a second imaging mode for counting detection events of the radiation imaging system is defined. The first imaging mode has a first counting scheme. The second imaging mode has a second counting scheme different than the first counting scheme. For example, the first counting scheme counts detection events corresponding to a set of radiation events different than the second counting scheme.

The first counting scheme and the second counting scheme may be selected from a group comprising of a first scheme, a second scheme, a third scheme, and a fourth scheme. The first scheme specifies that a secondary detection event, detected by a secondary detector cell, is counted in a secondary counter associated with the secondary detector cell (e.g., where the primary counter may be used herein to refer to a counter of a primary detector cell and the secondary counter is used herein to refer to a counter of a secondary detector cell). The second scheme specifies that the secondary detection event is counted in a primary counter associated with a primary detector cell instead of the secondary counter associated with the secondary detector cell. The third scheme specifies that a corresponding primary detection event is counted by the primary detector cell and that the secondary detection event is not counted unless the primary detection event and the secondary detection event occur within the same cell. The fourth scheme specifies that a first energy associated with the secondary detection event is to be merged with a secondary energy associated with the corresponding primary detection event to generate a merged energy. In this way, a plurality of imaging modes for counting detection events are defined.

The example method 700 ends at 708.

Figure 8:
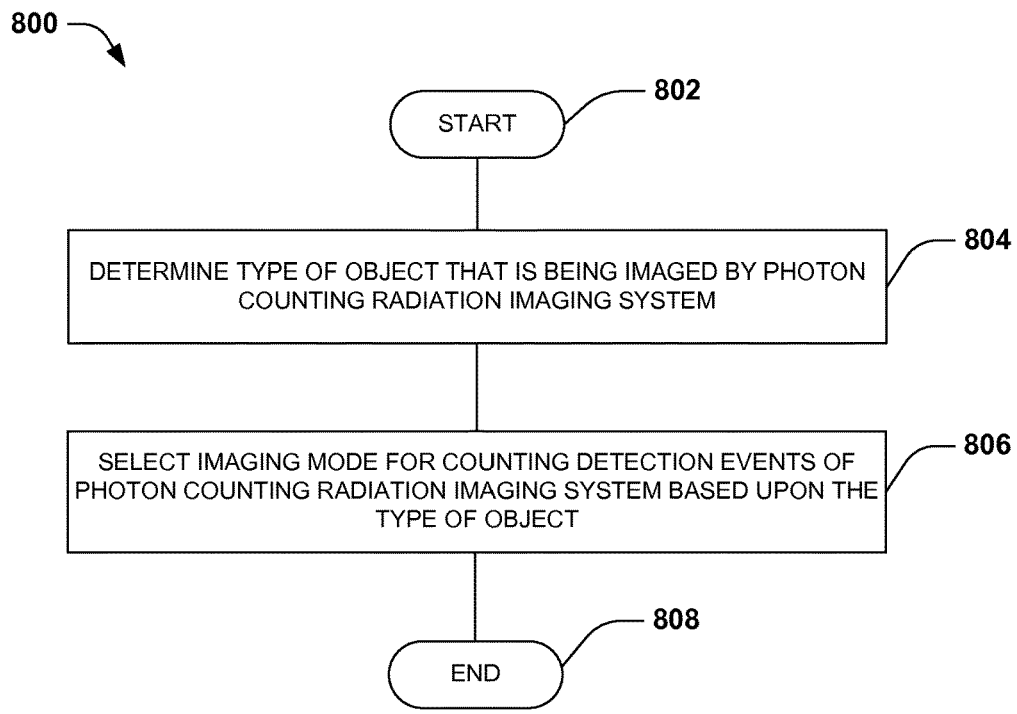
FIG. 8 is a flow diagram illustrating an example method for operation of a photon counting radiation imaging system.

Referring to FIG. 8, a flow diagram of an example method 800 for operation of a photon counting imaging system is provided.

The example method 800 starts at 802, and a type of object that is being imaged by the photon counting radiation imaging system may be determined, at 804. In an example, the type of object may be determined based upon a pre-scan of the object (e.g., the pre-scan may identify blood vessels, a central vein, and vein branches of a lung). In another example, a previously acquired image of the object may be analyzed to determine the type of object (e.g., object recognition may be perform upon the previously acquire image to identify a brain). In another example, the type of object may be determined based upon user input (e.g., the user may specify that a human heart is to be scanned by the photon counting radiation imaging system).

At 806, an imaging mode may be selected for counting detection events of the photon counting radiation imaging system based upon the type of object. In an example, the first imaging mode may be configured to generate images having a first spatial resolution. The second imaging mode may be configured to generate images having a second spatial resolution different than the first spatial resolution. The imaging mode is selected based upon a desired spatial resolution of images depicting the object. In another example, the imaging mode may be selected based upon a sensitivity to radiation associated with the type of object.

In another example, the first imaging mode is selected when the type of object corresponds to a first type of object (e.g., a heart). The second imaging mode is selected when the type of object corresponds to a second type of object (e.g., a brain). The first imaging mode has a first counting scheme and the second imaging mode has a second counting scheme different than the first counting scheme. The first counting scheme and the second counting scheme may be selected from a group comprising a first scheme, a second scheme, a third scheme, and a fourth scheme. The first scheme specifies that a secondary detection event, detected by a secondary detector cell, is counted in a secondary counter associated with the secondary detector cell. The second scheme specifies that the secondary detection event is counted in a primary counter associated with a primary detector cell instead of the secondary counter associated with the secondary detector cell. The third scheme specifies that a corresponding primary detection event is counted by the primary detector cell and that the secondary detection event is not counted unless the primary detection event and the secondary detection event occur within the same cell. The fourth scheme specifies that a first energy associated with the secondary detection event is to be merged with a secondary energy associated with the corresponding primary detection event to generate a merged energy. Different schemes may provide different image scanning characteristics. For example, the first scheme may provide low spatial resolution and high dose savings. The second scheme may provide medium spatial resolution and high dose savings.

The third scheme may provide high spatial resolution and medium dose savings. The fourth scheme may provide high spatial resolution, low dose savings, and spectral ability.

The example method 800 ends at 808.

Figure 9:
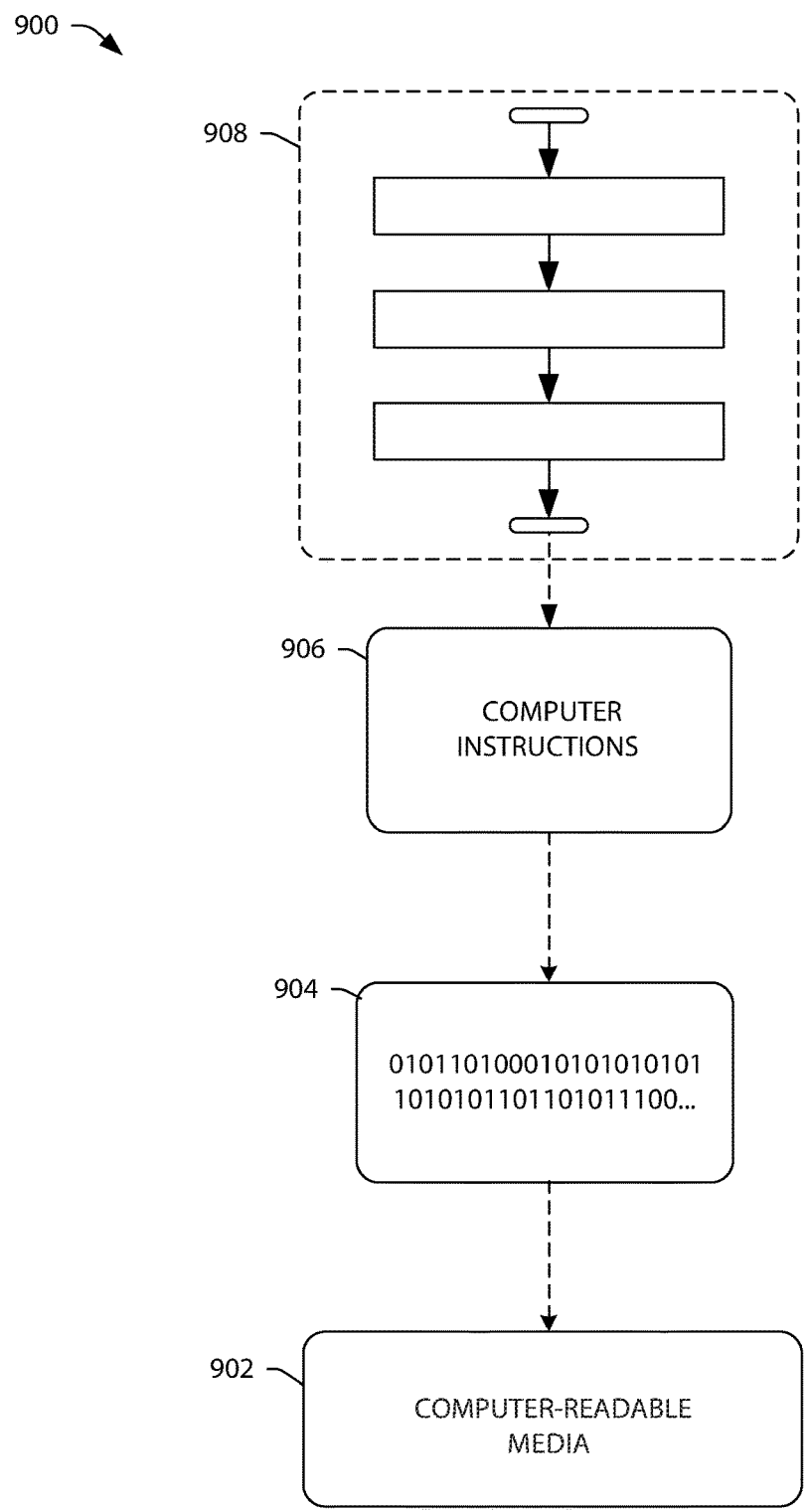
FIG. 9 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 9, wherein the implementation 900 comprises a computer-readable medium 902 (e.g., a flash drive, CD-R, DVD-R, application-specific integrated circuit (ASIC), field-programmable gate array (FPGA), a platter of a hard disk drive, etc.), on which is encoded computer-readable data 904. This computer-readable data 904 in turn comprises a set of processor-executable instructions 906 configured to operate according to one or more of the principles set forth herein. In one such embodiment of implementation 900, the processor-executable instructions 906 may be configured to perform a method 908 when executed via a processing unit, such as at least some of the example method 700 of FIG. 7 and/or example method 800 of FIG. 8. In another such embodiment, the processor-executable instructions 906 may be configured to implement a system, such as at least some of the example system 100 of FIG. 1 and/or the example system 200 of FIG. 2. Many such computer-readable media may be devised by those of ordinary skill in the art that are configured to operate in accordance with one or more of the techniques presented herein. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or." In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used, such terms are intended to be inclusive in a manner similar to the term "comprising." The claimed subject matter may be implemented as a method, apparatus, or article of manufacture (e.g., as software, firmware, hardware, or any combination thereof).

As used in this application, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc., for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the drawings. The disclosure includes all such modifications and alterations and is limited only by the scope of the claims. In particular regard to the various functions performed by the above-described components (e.g., elements, resources, etc.), the terms used to describe such components are intended to correspond, unless otherwise indicated, to any component that performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method for operation of a photon counting radiation imaging system, comprising:
   displaying a set of image scanning characteristics;
   receiving a user-selected value for each image scanning characteristic of the set of image scanning characteristics;
   selecting an imaging mode for examination of an object prior to the examination of the object based upon the user-selected value for each image scanning characteristic, wherein the imaging mode is selected from a group of imaging modes comprising:
      a first imaging mode defining a first counting scheme for counting detection events of a photon counting radiation imaging system, and a second imaging mode defining a second counting scheme for counting detection events of the photon counting radiation imaging system, wherein the second counting scheme is different than the first counting scheme;

defining a dose of radiation to be applied to the object based upon the imaging mode selected for the examination of the object; and performing the examination of the object after the selecting an imaging mode and the defining a dose, wherein:
during the examination the object is exposed to the dose of radiation defined based upon the imaging mode selected for the examination of the object, and
detection events occurring during the examination are counted according to a counting scheme associated with the imaging mode selected for the examination of the object.

2. The method of claim 1, wherein the first counting scheme is configured to count a secondary detection event, detected by a secondary detector cell, in a secondary counter associated with the secondary detector cell.

3. The method of claim 2, wherein the second counting scheme is configured to count the secondary detection event in a primary counter associated with a primary detector cell instead of the secondary counter associated with the secondary detector cell.

4. The method of claim 2, wherein the second counting scheme is configured to not count the secondary detection event.

5. The method of claim 2, wherein the second counting scheme is configured to determine a first energy associated with the secondary detection event and a second energy associated with a corresponding primary detection event and to merge, at a primary detector cell, the first energy associated with the secondary detection event and the second energy associated with the corresponding primary detection event to generate a merged energy.

6. The method of claim 5, wherein the second counting scheme is configured to not count the secondary detection event in the secondary counter associated with the secondary detector cell.

7. The method of claim 1, wherein the first counting scheme and the second counting scheme are selected from the group consisting of:
a first scheme in which a secondary detection event, detected by a secondary detector cell, is counted in a secondary counter associated with the secondary detector cell;
a second scheme in which the secondary detection event is counted in a primary counter associated with a primary detector cell instead of the secondary counter associated with the secondary detector cell;
a third scheme in which a corresponding primary detection event is counted by the primary detector cell and the secondary detection event is not counted; and
a fourth scheme in which:
a first energy associated with the secondary detection event is determined;
a second energy associated with the corresponding primary detection event is determined; and
the first energy associated with the secondary detection event and the second energy associated with the corresponding primary detection event is merged to generate a merged energy.

8. The method of claim 1, wherein for a set of radiation events, the first counting scheme counts detection events corresponding to the set of radiation events different than the second counting scheme.

9. A method for operation of a photon counting radiation imaging system, comprising:
determining a type of object that is being imaged by the photon counting radiation imaging system;
selecting an imaging mode for counting detection events of the photon counting radiation imaging system based upon the type of object;
defining a dose of radiation to be applied to an object based upon the imaging mode selected for counting detection events; and
performing an examination of the object after the selecting an imaging mode and the defining a dose, wherein:
during the examination the object is exposed to the dose of radiation defined based upon the imaging mode selected for counting detection events, and
detection events occurring during the examination are counted according to the imaging mode selected for counting detection events.

10. The method of claim 9, wherein the selecting comprises:
selecting a first imaging mode when the type of object corresponds to a first type of object; and
selecting a second imaging mode when the type of object corresponds to a second type of object, wherein the first imaging mode has a first counting scheme and the second imaging mode has a second counting scheme different than the first counting scheme.

11. The method of claim 10, wherein the first counting scheme and the second counting scheme are selected from the group consisting of:
a first scheme in which a secondary detection event, detected by a secondary detector cell, is counted in a secondary counter associated with the secondary detector cell;
a second scheme in which the secondary detection event is counted in a primary counter associated with a primary detector cell instead of the secondary counter associated with the secondary detector cell;
a third scheme in which a corresponding primary detection event is counted by the primary detector cell and the secondary detection event is not counted; and
a fourth scheme in which:
a first energy associated with the secondary detection event is determined;
a second energy associated with the corresponding primary detection event is determined; and
the first energy associated with the secondary detection event and the second energy associated with the corresponding primary detection event is merged to generate a merged energy.

12. The method of claim 9, wherein the determining comprises:
determining the type of object based upon user input.

13. The method of claim 9, wherein the determining comprises determining the type of object based upon a pre-scan of the object prior to the performing an examination.

14. The method of claim 9, wherein the determining comprises analyzing a previously acquired image of the object to determine the type of object.

15. The method of claim 9, wherein the selecting comprises selecting the imaging mode based upon a desired spatial resolution of images depicting the object.

16. The method of claim 9, wherein the selecting comprises selecting the imaging mode based upon a sensitivity to radiation associated with the object.

17. The method of claim 10, wherein the first imaging mode is configured to generate images having a first spatial resolution and the second imaging mode is configured to generate images having a second spatial resolution different than the first spatial resolution.

18. A photon counting radiation imaging system, comprising:
- a radiation source configured to emit radiation;
- a detector array comprising a plurality of detector cells respectively configured to count detection events;
- a mode selection component configured to select an imaging mode for the detector cells based upon user-input values for a plurality of image scanning characteristics, wherein a first imaging mode has a first counting scheme and a second imaging mode has a second counting scheme different than the first counting scheme; and
- a controller configured to determine a dose of radiation emitted by the radiation source based upon the imaging mode that is selected by the mode selection component.

19. The photon counting radiation imaging system of claim 18, wherein the first counting scheme and the second counting scheme are selected from the group consisting of:

- a first scheme in which a secondary detection event, detected by a secondary detector cell, is counted in a secondary counter associated with the secondary detector cell;
- a second scheme in which the secondary detection event is counted in a primary counter associated with a primary detector cell instead of the secondary counter associated with the secondary detector cell;
- a third scheme in which a corresponding primary detection event is counted by the primary detector cell and the secondary detection event is not counted; and
- a fourth scheme in which:
  - a first energy associated with the secondary detection event is determined;
  - a second energy associated with the corresponding primary detection event is determined; and
  - the first energy associated with the secondary detection event and the second energy associated with the corresponding primary detection event is merged to generate a merged energy.

20. The method of claim 1, wherein the first counting scheme counts a single radiation event as a single detection event and the second counting scheme counts the single radiation event as two detection events.

* * * * *